(12) United States Patent
Yano et al.

(10) Patent No.: US 9,116,123 B2
(45) Date of Patent: Aug. 25, 2015

(54) GLOSS MEASURING DEVICE AND IMAGE FORMING DEVICE INCLUDING SAME

(71) Applicants: So Yano, Ibaraki (JP); Naotoshi Kawai, Toyokawa (JP); Yoshiyuki Toso, Toyokawa (JP); Noboru Oomoto, Toyokawa (JP); Shoichi Yoshikawa, Okazaki (JP); Takao Miyamoto, Nagoya (JP)

(72) Inventors: So Yano, Ibaraki (JP); Naotoshi Kawai, Toyokawa (JP); Yoshiyuki Toso, Toyokawa (JP); Noboru Oomoto, Toyokawa (JP); Shoichi Yoshikawa, Okazaki (JP); Takao Miyamoto, Nagoya (JP)

(73) Assignee: KONICA MINOLTA BUSINESS TECHNOLOGIES, INC., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/795,773

(22) Filed: Mar. 12, 2013

(65) Prior Publication Data

US 2013/0250279 A1    Sep. 26, 2013

(30) Foreign Application Priority Data

Mar. 26, 2012 (JP) ................. 2012-069034

(51) Int. Cl.
*G01N 21/55* (2014.01)
*G01N 21/57* (2006.01)

(52) U.S. Cl.
CPC ....................................... *G01N 21/57* (2013.01)

(58) Field of Classification Search
USPC ........ 356/445, 446, 448, 237.2, 239.7, 243.4, 356/513, 514, 369, 152.2, 600, 612
See application file for complete search history.

(56) References Cited

U.S. PATENT DOCUMENTS

| 5,925,889 A * | 7/1999 | Guillory et al. .......... 250/559.16 |
| 6,792,161 B1 * | 9/2004 | Imaizumi et al. ............. 382/275 |
| 2006/0256341 A1 * | 11/2006 | Kuwada ........................ 356/445 |
| 2011/0222065 A1 * | 9/2011 | Imura ........................... 356/445 |

FOREIGN PATENT DOCUMENTS

| JP | 02-035339 A | 2/1990 |
| JP | 10-253534 A | 9/1998 |
| JP | 2000-131243 A | 5/2000 |
| JP | 2002-031921 A | 1/2002 |
| JP | 2002-214964 A | 7/2002 |
| JP | 2003-186260 A | 7/2003 |
| JP | 2006-267165 A | 10/2006 |
| JP | 2009-068891 A | 4/2009 |
| JP | 2009-271273 A | 11/2009 |

OTHER PUBLICATIONS

Office Action (Notification of Reasons for Refusal) dated Apr. 22, 2014, issued in corresponding Japanese Patent Application No. 2012-069034 with an English translation thereof. (5 pgs).

* cited by examiner

*Primary Examiner* — Tri T Ton
(74) *Attorney, Agent, or Firm* — Buchanan Ingersoll & Rooney PC

(57) ABSTRACT

A gloss measuring device that measures a gloss of an image formed on a sheet which is being transported, the gloss measuring device includes a light emission portion that emits light toward the sheet, a light reception portion that receives the light reflected specularly off the image formed on the sheet, and a position adjustment unit that performs adjustment such that the sheet being transported is in a measurement reference position.

8 Claims, 2 Drawing Sheets

GLOSS MEASURING DEVICE AND IMAGE FORMING DEVICE INCLUDING SAME

This application is based on Japanese Patent Application No. 2012-069034 filed on Mar. 26, 2012, the contents of which are hereby incorporated by reference.

BACKGROUND OF THE INVENTION

1. Field of the Invention

The present invention relates to a gloss measuring device and the like, and more particularly relates to a device that measures the gloss of an image formed on a sheet which is being transported and the like.

2. Description of the Related Art

In an electrophotographic image forming device such as a facsimile, a printer or a copying machine, especially in an image forming device used in the field of product printing, the stability of an image is highly required. Since, in recent years, it has been known that the gloss of an image somewhat affects its hue, in order to enhance the stability of an image, an operation of measuring the gloss of a formed image within a device to adjust image formation conditions and fixing conditions has been just started.

For example, in patent documents 1 to 4 (Japanese Unexamined Patent Application Publications Nos. 2002-31921, 2003-186260, 2006-267165 and 2009-68891), a technology is proposed in which the gloss of the surface of a developer image fixed on a recording medium after fixing is measured and image formation conditions and fixing conditions are controlled according to the results of the measurements.

For example, as specified in "JIS Z 8741," the gloss of a toner image is determined by measuring the amount of light that is specularly reflected and received among light applied to the toner image. Hence, when the gloss of a toner image on an unstable sheet that is being transported is measured, since the distance from a measurement portion to the sheet and the inclination of the sheet are changed, it is difficult to obtain a high measurement accuracy.

SUMMARY OF THE INVENTION

A gloss measuring device that measures a gloss of an image formed on a sheet which is being transported, the gloss measuring device includes a light emission portion that emits light toward the sheet, a light reception portion that receives the light reflected specularly off the image formed on the sheet, and a position adjustment unit that performs adjustment such that the sheet being transported is in a measurement reference position.

DESCRIPTION OF PREFERRED EMBODIMENTS

A gloss measuring device and an image forming device according to the present invention will be described below with reference to accompanying drawings; however, the present invention is not limited to these embodiments at all.

Figure 1:
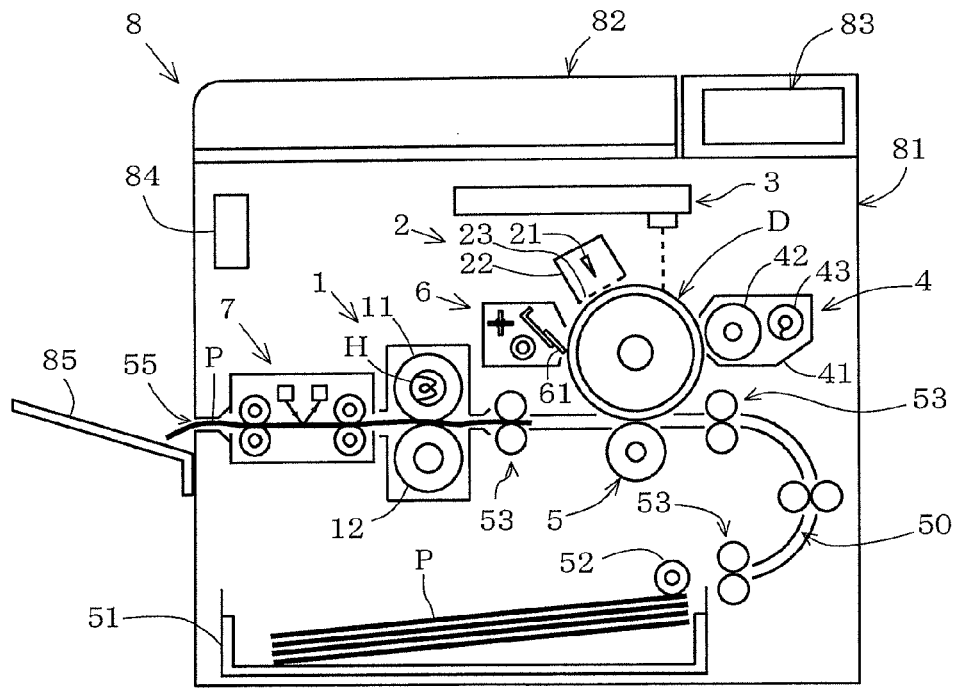
FIG. 1 A schematic diagram showing an example of an image forming device and a gloss measuring device according to the present invention.

FIG. 1 shows a schematic configuration diagram showing an embodiment of the image forming device according to the present invention. The image forming device 8 shown in FIG. 1 includes: a printer portion 81 that forms an image; an image reader portion 82 that reads an original document image; and an operation display portion 83 through which a user inputs image formation conditions and on which the state of the device and the like are displayed. The image reader portion 82 is a known image reader that reads an original document placed on an unillustrated original document glass plate by moving a scanner; image data that is converted into electrical signals with an unillustrated CCD image sensor can be obtained.

Around a cylindrical photosensitive member (electrostatic latent image carrying member) D that carries a toner image and rotates clockwise, the printer portion 81 is provided with: a charging device 2 that uniformly changes the surface of the photosensitive member D; an exposure device 3 that applies light to the surface of the photosensitive member D to form an electrostatic latent image; a development device 4 that supplies a toner to the photosensitive member D and develops the electrostatic latent image on the photosensitive member D to form the toner image; a transfer roller (transfer device) 5 that transfers the toner image on the photosensitive member D formed by the development device 4 to a sheet P; and a cleaning device 6 that removes the toner which has been left on the photosensitive member D without being transferred to the sheet P.

The charging device 2 is a scorotron charging device, and includes: a box-shaped shield electrode 22 in which a surface side opposite the photosensitive member D is open; a discharge electrode 21 which is placed in a tensioned state within the shield electrode 22; and a grid electrode 23 which is attached to the opening of the shield electrode 22. A voltage of a few thousand volts is applied to the discharge electrode 21 to produce a corona discharge, and thus the surface of the photosensitive member D is uniformly charged. The type of charging device 2 is not particularly limited; a roller system charging member, a blade-shaped charging member, a brush-shaped charging member or the like may be used.

The exposure device 3 selectively applies, based on, for example, image data input from an external device such as a personal computer, light to the surface of the photosensitive member D uniformly charged by the charging device 2 to perform exposure and forms a predetermined electrostatic latent image on the surface of the photosensitive member D.

The development device 4 includes a housing 41, a development roller 42 that is rotatably provided opposite the photosensitive member D and a transport roller 43 that transports a developer toward the development roller 42. Within the housing 41, the developer composed of the toner and a carrier (both of which are not shown) is held. When a development bias voltage is applied to the development roller 42, a potential difference between the voltage applied to the development roller 42 and the voltage of the electrostatic latent image on the photosensitive member D causes the toner to be moved to the photosensitive member D, and the electrostatic latent image on the photosensitive member D is visualized (toner image) by the toner.

The transfer roller 5 is provided such that the transfer roller 5 can be rotated by a drive motor (not shown) coupled to the transfer roller 5, and is pressed onto the photosensitive member D by a force application member (not shown). A transfer bias voltage whose polarity is opposite to the charging polarity of the toner is applied to the transfer roller 5 by an unillustrated voltage application unit. When the sheet P passes through between the photosensitive member D and the transfer roller 5, the transfer bias voltage is applied to the transfer roller 5 to transfer the toner image formed on the photosensitive member D to the sheet P.

The cleaning device 6 includes a cleaning blade 61 that is pressed onto the photosensitive member D, and removes, from the photosensitive member D, the toner that is left on the surface of the photosensitive member D without being transferred.

In a lower portion of the printer portion 81, a paper feed cassette 51 holding the sheets P is so arranged as to be removable from the printer portion 81. The sheets P held within the paper feed cassette 51 are sequentially fed to a transport path 50 one by one from the uppermost sheet by the rotation of a paper feed roller 52 arranged in an upper side portion of the paper feed cassette 51. The sheet P fed from the paper feed cassette 51 is transported to a resist roller pair 53 and is fed from the resist roller pair 53 to a nip portion between the transfer roller 5 and the photosensitive member D according to timing corresponding to the rotation of the photosensitive member D, and then the toner image is transferred to the sheet P as described above.

Furthermore, the printer portion 81 includes a fixing device 1 that fixes the toner image transferred from the photosensitive member D to the sheet P. The fixing device 1 includes a fixing roller 11 incorporating a halogen heater H and a pressurization roller 12 that is pressed onto the fixing roller 11. When the sheet P passes through a nip portion between the fixing roller 11 and the pressurization roller 12, the sheet P is heated and pressurized, and thus the toner image is fused and fixed to the sheet P. Then, the sheet P passes through a gloss measuring device 7 and is ejected through an ejection port 55 to a paper ejection tray 85 on the side surface of the main body.

The image forming device 8 includes a control device 84 that comprehensively controls constituent elements related to the image forming device 8; the control device 84 controls the drive and rotation of the photosensitive member D, the development roller 42, the transfer roller 5, the paper feed roller 52, the transport roller 53, the fixing roller 11 and the like and the operation of the charging device 2, the exposure device 3, the development device 4 and the like, also controls the transport speed of the fixing roller 11 and the turning on and off of the halogen heater H based on the measurement value of the gloss measuring device 7, which will be described later and adjusts the gloss of the toner image formed on the sheet P. Naturally, the control operation of the control device 84 is also performed by setting conditions input by the user through the operation display portion 83.

Figure 2:
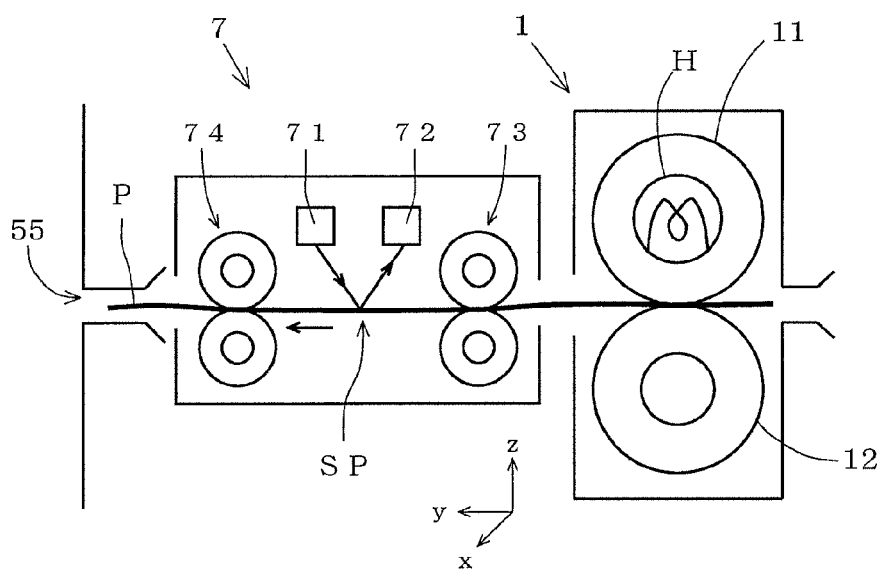
FIG. 2 An enlarged configuration diagram of a fixing device and the gloss measuring device in the image forming device of FIG. 1.

FIG. 2 shows a schematic configuration diagram of the gloss measuring device 7. The gloss measuring device 7 is provided on the downstream with respect to the fixing device 1 in the sheet transport direction, and includes: a light emission portion 71 that applies light toward a measurement reference position SP; a light reception portion 72 that receives the light reflected specularly (an incident angle and a reflection angle are equal) off the toner image formed on the sheet P; and a first transport roller pair 73 and a second transport roller pair 74 that serve as a position adjustment unit provided on the upstream side and the downstream side with respect to the measurement reference position SP in the sheet transport direction.

Since the sheet P is unstable during transportation, in a normal device, the sheet P is displaced in the X, Y and Z directions of the figure in the measurement reference position SP. Since the sheet P is displaced in any of the X, Y and Z directions of the figure, and thus the light specularly reflected off the toner image does not properly enter the light reception portion 72, it is impossible to highly accurately measure the gloss of the toner image.

Hence, in the gloss measuring device of the present invention, the first transport roller pair 73 and the second transport roller pair 74 that nip and transport the sheet P are provided, and the transport speed of the second transport roller pair 74 is set higher than that of the first transport roller pair 73. Thus, the sheet P is brought into a tensioned state in the measurement reference position SP, and is located in position in the X, Y and Z directions of the figure. The difference between the transport speeds of the second transport roller pair 74 and the first transport roller pair 73 is not particularly limited; in normal, it preferably falls within a range of 5 mm/sec. to 30 mm/sec. Although the second transport roller pair 74 needs to be drive rollers, the first transport roller pair 73 may be driven rollers.

The light applied from the light emission portion 71 to the toner image on the sheet P is not particularly limited as long as the light is parallel light; although the light may be either visible light or infrared light, in order to prevent variations in measurement sensitivity caused by the colors of the toner image, light other than visible light is preferably used, and light having a near-infrared wavelength is more preferably used.

The diameter of a spot of light, in the measurement reference position SP, applied from the light emission portion 71 to the sheet P is preferably 5 mm or more. The diameter of the spot is set at 5 mm or more, and thus it is possible to reduce the influences of high-frequency components caused by projections and recesses in the surface of the sheet P and low-frequency components caused by the curved surface of the sheet P, with the result that it is possible to more highly accurately measure the gloss.

The gloss value of the toner image measured by the gloss measuring device 7 is fed to the control device 84 (shown in FIG. 1), and, in order for a desired gloss to be obtained, fixing conditions such as the drive and rotation of the fixing roller 11 and a fixing temperature and image formation conditions such as the development bias voltage and the transfer bias voltage are adjusted.

Figure 3:
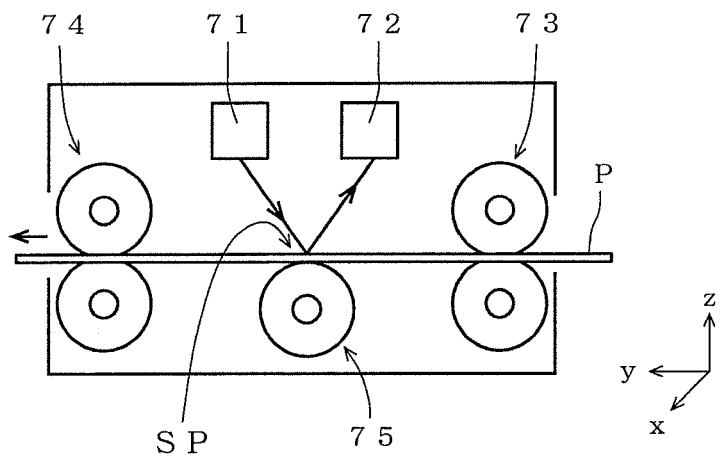
FIG. 3 A schematic diagram showing another embodiment of the gloss measuring device according to the present invention.

FIG. 3 shows another embodiment of the gloss measuring device according to the present invention. The same members and portions as in the embodiment described above are identified with the same symbols. The gloss measuring device shown in FIG. 3 includes: the light emission portion 71 that applies light toward the measurement reference position SP; the light reception portion 72 that receives the light reflected specularly off the toner image formed on the sheet P; and the first transport roller pair 73 and the second transport roller pair 74 that serve as the position adjustment unit provided on the upstream side and the downstream side with respect to the measurement reference position SP in the sheet transport direction. The gloss measuring device further includes a support roller (support member) 75 that makes contact with and supports the sheet P in the measurement reference position SP.

When the sheet P is nipped and transported by the first transport roller pair 73 and the second transport roller pair 74, the support roller 75 is made to make contact with and support the back surface of the sheet P, and thus the sheet P is located in position in the X, Y and Z directions of the figure in the measurement reference position SP. Thus, it is possible to highly accurately measure the gloss.

The support member that makes contact with and supports the back surface of the sheet P in the measurement reference position SP preferably has a material and a shape having a low frictional resistance to the sheet P; the support member may be formed in the shape of a roller, a plate or the like. The support member may be able to be moved to a position where it makes contact with the sheet P or to a position where it does not make contact with the sheet P. Specifically, after an end of the sheet P is nipped by the nip portion of the second transport roller pair 74, that is, when the sheet P is nipped by the first transport roller pair 73 and the second transport roller pair 74, the support member may be moved from the non-contact position to the contact position to support the sheet P.

Figure 4:
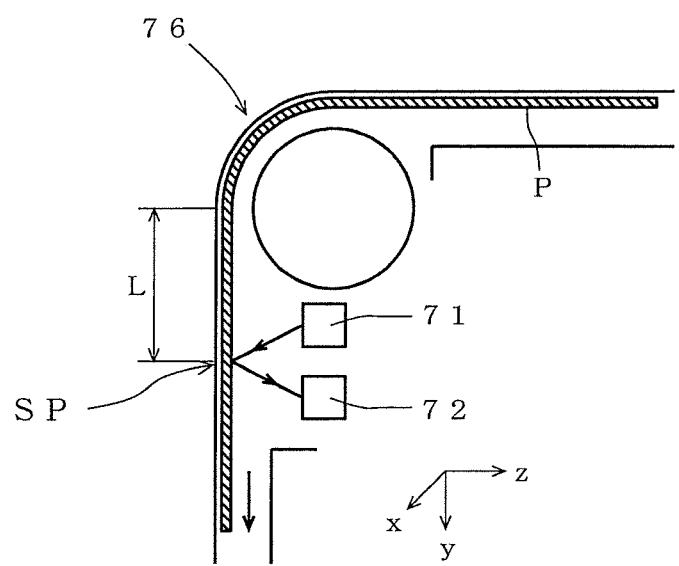
FIG. 4 A schematic diagram showing yet another embodiment of the gloss measuring device according to the present invention.

FIG. 4 shows yet another embodiment of the gloss measuring device according to the present invention. In the gloss measuring device shown in FIG. 4, in the transport path on the upstream side with respect to the measurement reference position SP in the sheet transport direction, a bent portion (position adjustment unit) 76 that bents the sheet transport direction at an approximate right angle is provided. The sheet transport direction is bent by the bent portion 76, and thus the sheet P that has passed through the bent portion 76 is attached to the inner surface of the transport path by the rigidity of the sheet P, with the result that the sheet P is located in position in the X, Y and Z directions of the figure in the measurement reference position SP. Thus, it is possible to highly accurately measure the gloss.

The angle at which the sheet transport direction is bent by the bent portion 76 is not particularly limited as long as the sheet P that has passed through the bent portion 76 is attached to the inner surface of the transport path by the rigidity of the sheet P; the angle is preferably determined as necessary from the type, size and the like of sheet P. In normal, the bending angle preferably falls within a range of 30° to 100°.

The distance L from the bending completion end of the bent portion 76 to the measurement reference position SP is preferably determined as necessary from the type and the like of sheet P; in normal, the distance L is preferably about a few centimeters.

According to the above gloss measuring device of the present invention, it is possible to highly accurately measure the gloss of an image on a sheet which is being transported.

According to the above image forming device of the present invention, it is possible to stably obtain an image of desired gloss and hue.

What is claimed is:

1. A gloss measuring device that measures a gloss of an image formed on a sheet which is being transported, the gloss measuring device comprising:
   a light emission portion that emits light toward the sheet;
   a light reception portion that receives the light reflected specularly off the image formed on the sheet; and
   a position adjustment unit that performs adjustment such that the sheet being transported is in a measurement reference position, said the position adjustment unit including an upstream transport roller pair and a downstream transport roller pair provided on respective upstream and downstream sides of the measurement reference position in a sheet transport direction, wherein
   said upstream transport roller pair and said downstream transport roller pair are configured to nip and transport the sheet and are controlled such that they bring the sheet into a tensioned state therebetween,
   a transport speed of the downstream transport roller pair on the downstream side in the sheet transport direction is set higher than a transport speed of the upstream transport roller pair on the upstream side in the sheet transport direction, and
   the gloss measuring device measures the gloss of the image formed on the sheet being transported.

2. The gloss measuring device of claim 1,
wherein a diameter of a spot of the light, in the measurement reference position, applied from the light emission portion to the sheet is 5 mm or more.

3. The gloss measuring device of claim 1,
wherein the light applied from the light emission portion to the sheet is near-infrared light.

4. The gloss measuring device of claim 1, wherein
the position adjustment unit further includes a support member that makes contact with and supports the sheet in the measurement reference position, and
while the sheet is supported by the support member, the gloss measuring device measures the gloss of the image formed on the sheet being transported.

5. An image forming device comprising:
the gloss measuring device of claim 1.

6. The image forming device of claim 5,
wherein a diameter of a spot of the light, in the measurement reference position, applied from the light emission portion to the sheet is 5 mm or more.

7. The image forming device of claim 5,
wherein the light applied from the light emission portion to the sheet is near-infrared light.

8. The image forming device of claim 5, wherein
the position adjustment unit further includes a support member that makes contact with and supports the sheet in the measurement reference position, and
while the sheet is supported by the support member, the gloss measuring device measures the gloss of the image formed on the sheet being transported.

\* \* \* \* \*